(12) United States Patent
Hodson et al.

(10) Patent No.: US 8,997,799 B2
(45) Date of Patent: Apr. 7, 2015

(54) POWDER FILLING PROCESSES

(75) Inventors: Peter D. Hodson, Derbyshire (GB);
Matthew J. Wilby, Leicestershire (GB)

(73) Assignee: Adamis Pharmaceuticals Corporation, San Diego, CA (US)

( * ) Notice: Subject to any disclaimer, the term of this patent is extended or adjusted under 35 U.S.C. 154(b) by 1659 days.

(21) Appl. No.: 12/293,683

(22) PCT Filed: Mar. 22, 2007

(86) PCT No.: PCT/US2007/064654
§ 371 (c)(1),
(2), (4) Date: Sep. 19, 2008

(87) PCT Pub. No.: WO2007/112267
PCT Pub. Date: Oct. 4, 2007

(65) Prior Publication Data
US 2010/0229859 A1   Sep. 16, 2010

(30) Foreign Application Priority Data
Mar. 23, 2006  (GB) .................................. 0605723.6

(51) Int. Cl.
*B65B 1/04*   (2006.01)
*B65B 1/30*   (2006.01)
(Continued)

(52) U.S. Cl.
CPC .......... *A61K 9/0075* (2013.01); *A61M 15/0051* (2013.01); *A61M 2202/064* (2013.01)

(58) Field of Classification Search
USPC ............. 141/131, 12, 125, 126, 129, 95, 198;
128/303.15; 264/171.1, 171.13, 259;
53/436, 473, 452, 453, 427, 559;
427/2.14, 2.31, 189, 194, 195, 201,
427/475, 482, 428.06, 428.18, 428.2;
118/304.308
See application file for complete search history.

(56) References Cited

U.S. PATENT DOCUMENTS 3,948,264 A   4/1976  Wilke et al.
3,971,377 A   7/1976  Damani
(Continued)

FOREIGN PATENT DOCUMENTS

EP   69715   6/1982
EP   79478   10/1982
(Continued)

OTHER PUBLICATIONS

'Drug Delivery to the Respiratory Tract' ed. D.Ganderton and T.Jones, publ. Ellis Horwood, Chichester (1987) pp. 89-90.

*Primary Examiner* — Jason Boeckmann
*Assistant Examiner* — Steven M Cernoch
(74) *Attorney, Agent, or Firm* — K&L Gates LLP; Louis C. Cullman; Robert W. Winn (57) ABSTRACT

A method for filling a plurality of microdepressions in a major surface of a web with finely divided powder in which the web is fed continuously to and through a powder filling stage including a driven roller. At the powder filling stage, the powder, which is fed either onto the web upstream of the roller or to the roller of the powder filling stage, is filled into the microdepressions of the web using the driven roller, wherein said roller is rotating about an axis generally transverse to the direction of web, while the surface speed of the roller and the web speed are different and wherein the roller and web are positioned relative to one another, such that between the upper surface of the web and the outer surface of the roller there is a gap. A method of manufacturing an elongate carrier with microdepressions containing finely divided powder comprising steps filling a plurality of microdepressions in a major surface of a web as described, removing from upper surface of the web excess powder not filled within the microdepressions and remaining on areas of the surface between the depressions, and optionally slitting and/or cutting the web in width and/or length.

15 Claims, 1 Drawing Sheet

(51) Int. Cl.
*B65B 43/42* (2006.01)
*A61K 9/00* (2006.01)
*A61M 15/00* (2006.01)

(56) References Cited

U.S. PATENT DOCUMENTS

| | | | |
|---|---|---|---|
| 4,088,093 A | 5/1978 | Pan | |
| 4,139,613 A | 2/1979 | Hefele | |
| 4,147,166 A | 4/1979 | Hansen | |
| 4,153,753 A | 5/1979 | Woodman et al. | |
| 4,197,289 A | 4/1980 | Sturzenegger | |
| 4,209,553 A | 6/1980 | Greenberg | |
| 4,288,521 A | 9/1981 | Kojima et al. | |
| 4,313,972 A | 2/1982 | Goller et al. | |
| 4,470,350 A | 9/1984 | Wright | |
| 4,789,569 A | 12/1988 | Douche et al. | |
| 4,800,102 A | 1/1989 | Takada | |
| 5,104,230 A | 4/1992 | Douche et al. | |
| 5,118,376 A | 6/1992 | Pigneul et al. | |
| 5,192,548 A | 3/1993 | Velasquez et al. | |
| 5,408,994 A | 4/1995 | Wass et al. | |
| 5,415,717 A | 5/1995 | Perneborn | |
| 5,437,271 A | 8/1995 | Hodson et al. | |
| 5,469,843 A | 11/1995 | Hodson | |
| 5,482,032 A | 1/1996 | Smith et al. | |
| 5,503,869 A | 4/1996 | Van Oort | |
| 5,569,484 A | 10/1996 | Muller et al. | |
| 5,619,984 A | 4/1997 | Hodson | |
| 5,655,523 A | 8/1997 | Hodson | |
| 5,682,733 A * | 11/1997 | Perrone | 53/560 |
| 5,699,649 A | 12/1997 | Abrams et al. | |
| 5,792,513 A | 8/1998 | Koslow et al. | |
| 5,897,746 A | 4/1999 | Attenberger et al. | |
| 5,960,609 A | 10/1999 | Abrams et al. | |
| 6,037,019 A | 3/2000 | Kooyer et al. | |
| 6,102,179 A | 8/2000 | Hodson et al. | |
| 6,146,685 A | 11/2000 | Chrai et al. | |
| 6,319,541 B1 | 11/2001 | Pletcher et al. | |
| 6,440,216 B1 * | 8/2002 | Aschenbeck | 118/308 |
| 6,652,903 B2 | 11/2003 | Muller | |
| 2002/0085977 A1 | 7/2002 | Fotland et al. | |
| 2004/0094229 A1* | 5/2004 | Danby et al. | 141/114 |

FOREIGN PATENT DOCUMENTS

| | | |
|---|---|---|
| EP | 166294 | 6/1985 |
| GB | 1479283 | 7/1973 |
| GB | 2102295 | 7/1982 |
| GB | 2144997 | 7/1984 |
| WO | WO 87/05213 | 9/1987 |
| WO | WO 92/19198 | 11/1992 |
| WO | WO 94/12230 | 6/1994 |
| WO | WO 95/21768 | 8/1995 |
| WO | WO 98/31346 | 7/1998 |
| WO | WO 03/077891 | 9/2003 |
| WO | WO 03/088944 | 10/2003 |
| WO | WO 2004/017914 | 3/2004 |

* cited by examiner

POWDER FILLING PROCESSES

CROSS REFERENCE TO RELATED APPLICATIONS

This application is a national stage filing under 35 U.S.C. 371 of PCT/US2007/064654, filed Mar. 22, 2007, which claims priority to Foreign Application No. 0605723.6, filed Mar. 23, 2006, the disclosure of which is incorporated by reference in its/their entirety herein.

The present application claims priority to GB Provisional Application Serial Number 0605723.6, filed Mar. 23, 2006.

FIELD

This invention relates to a process for filling finely divided powder into a plurality of microdepressions in the surface of a flexible web, as well as a method of manufacturing an elongate carrier with microdepressions containing finely divided powder. The filled web and/or elongate carrier can conveniently be used in the administration of biologically active substances, in particular medicaments by inhalation.

BACKGROUND

Asthma and other respiratory diseases have long been treated by the inhalation of appropriate medicament. For many years the two most widely used and convenient choices of treatment have been the inhalation of medicament from a drug solution or suspension in a pressurised metered dose inhaler (pMDI), or inhalation of powdered drug, generally admixed with an excipient, from a dry powder inhaler (DPI). Following strong concern about the link between depletion of the earth's ozone layer and chlorofluorocarbon (CFC) emissions, the use of these materials in pressurised inhalers is being phased out and interest in DPI systems has been stimulated.

Most DPIs use either bulk powder reservoirs or individual pre-measured doses. There are, however, problems associated with accurately metering a measured small quantity (e.g. 500 micrograms or less) of powder either from a bulk reservoir within an inhaler or into a capsule or blister. With many drugs, e.g. potent drugs, this introduces the necessity to add excipients, such as lactose powder, to significantly increase the quantity of powder to be metered. Such excipients are however generally undesirable as they can pose subsequent powder deagglomeration problems and can cause dryness and other unwanted effects in the patient's mouth.

Dry powder inhalers in which predetermined doses of medicament are dispensed from a sheet material including discrete microdepressions (having a depth of about 5 to 500 micron and an opening at the surface of the sheet material of about 10 to 500 micron in width) filled with medicament are disclosed in U.S. Pat. Nos. 5,408,994, 5,437,271, 5,469,843, 5,482,032, and 5,655,523.

Various methods for coating powders on to substrates are known. Typical of those under consideration for use in drug delivery applications are the electrostatic coating methods disclosed in U.S. Pat. Nos. 4,197,289, 5,699,649, 5,960,609, 6,146,685, 6,319,541 and 6,652,903, and US patent application US200210085977. Such methods tend to be complex, slow, and difficult to control.

Other methods of coating powders onto moving web substrates include fluidized bed methods, for example as disclosed in U.S. Pat. Nos. 4,088,093 and 6,037,019, spraying methods (e.g. U.S. Pat. Nos. 4,288,521 and 5,897,746), suction methods (e.g. U.S. Pat. No. 4,313,972), magnetic methods (e.g. U.S. Pat. No. 4,470,350), and sprinkling methods (e.g. U.S. Pat. Nos. 4,209,553 and 5,415,717). A method of depositing suspended particles onto a substrate for use in inhalation devices, involving suspending agent evaporation, is disclosed in U.S. Pat. No. 5,503,869. However, none of these various methods is well suited to the accurate metering of pharmaceutical powders into microdepressions on a surface of a web.

WO patent application 95/21768 describes a process for filling blister cavities with powder whilst they are mounted on a continuous web. An oscillating and rotating system is provided to break down aggregates in the 0.1 to 10 mg powder doses. Such large masses of powder are very many times greater than the small quantities of powder that the microdepressions tape based inhalers described in the aforementioned patents are intended to deliver.

U.S. Pat. No. 5,192,548 discloses a method of coating micronized drug onto a closed loop of sheet material including microdepressions on its top-side in which micronized drug is fed onto the sheet material, rollers assist in spreading micronized drug over the surface of the sheet material and curved slats function to smear the micronized drug out over the surface of the sheet material. One roller is shown with a flattened portion intended to help prevent drug from building up behind it.

SUMMARY OF THE INVENTION

There is an ongoing need in providing processes for accurately and uniformly filling microdepressions with finely divided powder (in particular biologically active substances, such as medicaments) and/or providing processes for manufacturing elongate carriers having microdepressions substantially accurately and uniformly filled with such finely divided powders, in particular such processes operating continuously and/or suitable for industrial scale use.

According to one aspect of the present invention there is provided a method for filling a plurality of microdepressions in a major surface of a web with finely divided powder in which the web is fed continuously to and through a powder filling stage including a driven roller. At the powder filling stage, the powder, which is fed either onto the web upstream of the roller or to the roller of the powder filling stage, is filled into the microdepressions of the web using the driven roller, wherein said roller is rotating about an axis generally transverse to the direction of web movement, while the surface speed of the roller and the web speed are different and wherein the roller and web are positioned relative to one another, such that between the upper surface of the web and the outer surface of the roller there is a gap.

Another aspect of the present invention is the provision of a method of manufacturing an elongate carrier with microdepressions containing finely divided powder comprising the process step of filling a plurality of microdepressions in a major surface of a web as described above and further comprising the step of removing from upper surface of the web excess powder not filled within the microdepressions and remaining on areas of the surface between the depressions. Additionally, if desired, the web with the filled microdepressions may be slit and/or cut in predetermined widths and/or predetermined lengths.

Surprisingly by applying different speeds to the driven roller's surface and to the web, and by positioning the roller and web relative to one another to provide a gap between the outer surface of the roller and the upper surface of the web, during the process operation of powder feeding and filling the outer surface of the roller forms a substantial covering of 
powder in the form of a visually uniform (e.g. visually uniform in smoothness and thickness) and continuous layer, which allows for desirably accurate and uniform filling of the microdepressions. The formation of a stable, substantial covering of powder on the roller is desirably facilitated through the application of a gap width of 1.25 mm or less. The application of a gap width of 0.2 mm or greater is desirable for a stable and smooth filling process. Stable processes of uniform filling of powder into depressions of the moving web has been found for a fixed gap width, however an element of flexibility in positioning of the roller and web has been found to be advantageous, so that the gap is variable in width. For example to facilitate the prevention of the formation of high pressures at the roller, due to the powder accumulating at the gap, the positioning of roller and web may be arranged in such a way that the gap is biased towards a pre-determined minimum width, for example through the use of springs, but at the same allowing some variability in the gap width, e.g. movement towards a greater gap width.

The formation of a stable, substantial covering of powder on the roller is also, desirably, facilitated by rotating the roller in the same direction as the web movement. Further, the provision of a roller surface speed that is greater than the web speed has been found useful in maintaining a stable covering of powder on the roller during filing. A surface speed for the roller that is 1.1 or more times greater than the web speed has been found particularly useful.

For even further enhanced ease in filling as well as enhanced process reliability and stability, it has been found desirable to feed the web to the roller generally along a first plane and from the roller generally along a second plane, such that at the roller the web passes through a bend, wherein the first plane and the second plane define an angle of less than 180° towards the roller (referred to in the following as "contact angle"). While not wishing to be bound to a particular theory, it is believed that the provision of such a contact angle allows for a partial wrap around of the web at the roller providing a component of force directly normal to the powder coating on the roller.

Due to the desirable accuracy and uniformity of filling in processes in accordance with the invention, these processes are particular suited to filling webs and/or manufacturing elongate carriers filled with a biologically active substance. Moreover the filled webs and/or elongate carriers as provided by processes disclosed herein, including well-controlled metered and small quantities of a biologically active substance, may be advantageously utilized as such or as part of delivery systems for the administration of such powders comprising a biologically active substance or substances.

The dependent claims define further embodiments of the invention.

BRIEF DESCRIPTION OF DRAWINGS

The invention will now be described with reference to the accompanying drawings in which:

FIG. 1 represents a schematic illustration of an exemplary device for filling finely divided powder into microdepressions on a major surface of a web using an exemplary process in accordance with the invention.

FIG. 2 represents a schematic illustration of the feed of web to and from the roller illustrated in FIG. 1.

FIG. 3 represents a cross sectional view of a schematic of a web comprising a plurality of microdepressions.

DETAILED DESCRIPTION

It is to be understood that the present invention covers all combinations of particular, suitable, desirable, favorable, advantageous and preferred aspects of the invention described herein.

Referring to FIG. 1 providing a schematic illustration of an exemplary device (1) for filling finely divided powder into microdepressions of a web using an exemplary process in accordance with the invention, the web (8) is generally fed continuously to and through a powder filling stage (15). The web (8) may be fed from a roll (not shown).

Referring to FIG. 3, webs, for use in processes described herein, comprise a plurality of microdepressions (11) in a major surface of the web. Depressions (11) may be suitably truncated cones, but may alternatively be of any suitable configuration for holding finely divided powder including generally truncated pyramids, partial hemispheres and tetrahedrons and other geometric configurations as well as non-geometric configurations. Preferred depressions have a sidewall angle of about 15°-20° to the vertical when the major surface is horizontal. The plurality of depressions may be provided in a regular array, or alternatively the array of depressions may take any form or pattern and need not be regular (i.e. the array may be irregular in appearance). Desirably the microdepressions are discrete.

Depressions generally have a depth of about 5 to 500 microns and an opening at the surface of the web of about 10 to 500 microns in width. Depressions have a depth less than the thickness of the web, so that the depressions do not form pores extending through the entire thickness of the web. In the case of discrete depressions having generally circular openings such as truncated cones or partial hemispheres, for example, the width discussed above is, in fact, the diameter of the circular opening. Preferred depressions have a depth of about 5 to 150 micron and an opening (e.g., diameter in the case of discrete truncated cones or partial hemispheres or the like) at the surface of the sheet material of about 50 to 200 microns. Depressions may be suitably spaced at an interval of about 20 to 2000 microns, more suitably at an interval of about 300 to 2000 microns. Depressions may suitably number from about 25 to 1000 per $cm^2$ of the web. The volume of each depression and the spacing or number of the depressions will depend upon the particular desired application of the resulting filled web and/or elongate carrier, and in the case of biologically active substances (e.g. medicaments) the potency of the particular substance and the area of the sheet material intended to represent a single dose of the substance. Typically it is desirable that the web material has a substantially uniform depression volume per unit area when considered on a scale of the area of a single dose or other functional unit.

Depressions may be formed in a web material by any suitable technique such as micro-imprinting using a photolithographically-patterned magnesium alloy plate or other micro-machined plate. Other conventional techniques that may be used are optical imaging or laser imaging.

Webs for use in the processes described herein are generally flexible. The web may be a single (layer) material or a laminate including a layer affixed (e.g. laminated, bonded or extruded) onto a support layer. Support layers may be formed of paper, non-wovens, wovens, nettings or polymeric films, such as polyester films. Suitably the web, as a single material or as a layer thereof affixed to a support layer, may comprise a polymeric material (such as polyethylene, polypropylene, polyester, polytetrafluoroethylene or mixtures thereof, in particular polyethylene or polypropylene). For the filling of powders that are sensitive to moisture, it may be desirable to incorporate a dessicant material. Also, inorganic salts or well-dispersed conductive materials may also be incorporated into the web material to lessen any static charge which may build up on the web.

Generally webs, either formed of a single material or as a laminate, have a thickness of at least 25 microns. Webs having a thickness of at least 75 microns are more suitable and a thickness of at least 100 microns most suitable. Webs having a thickness of at most 1000 microns are generally suitable, while webs having a thickness of at most 750 microns are more suitable, at most 500 microns even more suitable and at most 250 microns most suitable. An example of suitable material for a single material web includes polypropylene, because polypropylene exhibits sufficient integrity and durability without the inclusion of a support layer. An example of a suitable laminated web includes polyethylene-coated kraft paper.

Returning to FIG. 1, the web (8) may be fed to a powder feeding stage (50) where finely divided powder (4) is fed onto the upper surface of the web, said surface comprising a plurality of microdepressions (not shown). Movement of the web in the general direction indicated by the arrow (10) then causes the powder on the web to travel with the web to the powder filling stage (15) including a driven roller (12).

Figure 1:
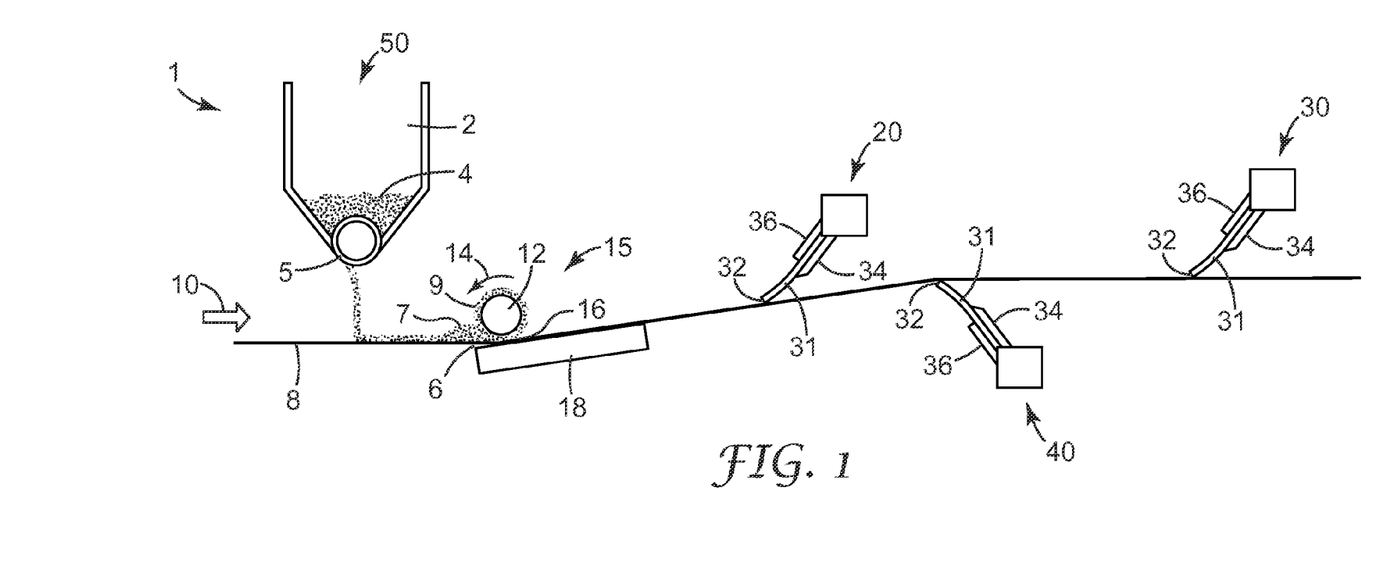

The powder feeding arrangement may be of any suitable form to feed powder either directly to the roller of the powder filling stage or onto the surface of the web upstream of the roller of the powder filling stage. FIG. 1 shows an exemplary representation of the latter type of powder feeding.

In the second type of powder feeding, powder may be provided for example onto the upper surface of the web upstream of a "nip" on the upstream side of the roller (e.g. near the gap below the roller of the powder filling stage). By allowing an excess of powder to accumulate as a bow wave at the nip, the bow wave can act as a reservoir, and ensure continuity and uniformity of the powder application process. Conveniently, powder may be fed to the nip by being dropped onto the moving web upstream of the roller and its bow wave. Alternatively, the powder may be fed (e.g. dropped) directly into the bow wave of powder just upstream of the roller of the powder filling stage. Such feeds of powder may be continuous or may be intermittent or varying in rate. Desirably the powder feeder arrangement is selected such that during powder feed, large agglomerates (e.g. 2 mm or larger) are not formed, for example to prevent large agglomerates reaching the nip which could lead to obstruction of further entry of powder into the nip region and/or disturbances in filling. Screw feed arrangements, vibrating sieve arrangements, and riffler (powdered sample divider) arrangements are examples of powder feed systems that may be suitable. Suitably the web is fed continuously to and through the powder feeder arrangement or stage. Conveniently, as shown in the schematic illustration of FIG. 1, a vibrating hopper (2) with a screw feed arrangement (5) may be used to feed (drop) powder (4) onto the web, as the web moves to and through the powder feeding stage (50).

The feed of powder need not be spread laterally across the web's width, but may be fed to just one part of the web's width, for example it may be fed to the center-line of the web. Once a sufficient accumulation of powder has built up as a bow wave on the top surface of the web at the roller, the powder tends to spread itself laterally. For a web width of about 150 mm, a single feed is typically satisfactory. For wider webs, or if lateral segregation of the powder within the bow wave of powder occurs (for example if coarser or finer particles of a particular powder substance have a tendency to move out to the edges of the web preferentially), then multiple feeds across the web may be employed. Alternatively, a single feed may be spread out to produce a wide lateral spread of powder onto the web top surface, by means of a spinning or reciprocating riffler or other suitable arrangement.

In regard to the alternative of feeding powder directly to the roller, here powder may be simply fed directly onto the roller, typically in through a gentle feed such that the continuous powder layer on the roller is maintained while being replenished. Alternatively, a wall arrangement downstream of the roller may be used to hold a reservoir of powder at the downstream side of the roller, from which the roller may pick up and feed (transport) powder over itself to its upstream nip where it may be incorporated into the continuous covering layer to maintain and replenish the layer. Here again it is desirable that the powder feed arrangement is selected such that it does not allow too great an excess of powder to disturb the layer on the roller nor allow large agglomerates to be fed to the roller and/or to the nip.

For both types of powder feeds, it is desirable that feeding of powder is carried out, as to provide an accumulation of powder on the web upstream of and adjacent to the roller (e.g. at the nip of the roller). Such an accumulation (for example in the form of a bow wave) can act as a reservoir of powder, replenishing the powder coating on the outer surface of the roller, and thus, aiding to ensure continuity and uniformity of the powder filling process. Processes described herein may desirably and additionally comprise automatic control means to switch on or off, or to vary the rate of, the powder feed. Moreover, the feeding of the powder may be desirably automatically controlled in response to a sensor or sensors, such a sensor or sensors sensing accumulation of powder (e.g. the presence and/or the quantity of powder) on the roller and/or accumulation of powder (e.g. the presence and/or the quantity of powder) on the web upstream of the roller, for example at the bow wave. For example, a sensor or sensors (e.g. capacitive sensor(s) or reflectance type opt-electronic sensor(s)) may conveniently be used to monitor the thickness of the covering layer of powder on the rotating roller. By adjustment of the sensitivity of such a sensor or sensors, depletion of this covering layer may be detected prior to it becoming sufficiently non-uniform or depleted to provide acceptable uniformity of coating, so that powder feed can be accordingly and automatically adjusted as to replenished the covering layer on the roller. In conjunction with this or alternatively thereto, it has been found advantageous to use a sensor or sensors (e.g. a capacitive sensor(s) or a transmittance type opto-electronic source/detector sensor(s)) to sense the quantity of powder accumulated upstream of the roller, for example at the bow wave. For example a transmittance type opto-electronic source/detector pair sensor arrangement has proved highly advantageous to detect the presence of such an accumulation of powder several millimeters in front of the leading edge of a 23 mm diameter roller. Such a sensor or sensors for the quantity of powder accumulation is/are well suited to monitor the quantity of powder and to provide automatic feedback for controlling the powder feed (e.g. switching on and off a powder feeder or varying the rate of powder feed, etc.). Generally for processes in which powder is fed onto the web surface upstream from the roller, it is desirable that the feeder is positioned fairly close to the roller, so that time delays in powder feed adjustments are minimized and hence control is suitably responsive.

Processes described herein may include a containment of powder on the web and at the roller. For example, this may conveniently be achieved by arranging vertical plates or metal shims on either side of the moving web of sheet material, in order to laterally confine the powder. (Vertical confinement is of course provided by the web itself and by gravity, and adequate longitudinal confinement is provided by motion of the web and by the nature of the process itself.) Desirably, the vertical plates may be gently biased against the edges of the web, to allow for differences in the lateral steering of the web with time whilst avoiding significant bending of the web. Conveniently, biased rubber sheets may be employed.

Again returning to FIG. 1 providing a schematic illustration of an exemplary process in accordance with the invention, it can be appreciated that the driven roller (12) of the powder filling stage (15) is rotating about an axis generally transverse to the direction of web movement. Desirably the roller is rotating in the same direction as that of the general web movement (as indicated by arrow (10)) and hence in the direction of the arrow (14). Furthermore, as can be appreciated from FIG. 1, there is a narrow gap (16) between the outer surface of roller (12) and the upper surface of web (8). In the exemplary embodiment of FIG. 1, the application of a solid base plate (18) underneath and appropriately spaced apart from the roller to form a passage (6) allows for a positioning of the roller (12) and web (8) relative to one another such that a gap (16) is provided between the outer surface of the roller and the upper surface (towards the roller) of the web. In particular, in the exemplary embodiment of FIG. 1, as the web (8) passes through the passage (6) between the roller (12) and the base (18), powder (4) on the web forms an accumulation (7) upstream of the roller (12) and the gap (16) is provided between the outer surface of the roller and the upper surface of the web. The positioning of the roller and the web relative to one another in order to provide a gap between the two can be achieved by other suitable means, such as replacing the illustrated base plate of FIG. 1 with other types of base elements (e.g. a series of non-driven rollers, belt arrangement, or a doctor blade or a second roller (which may or may not be driven)) opposite to the driven roller of the powder fill stage so as to provide a passage for the web between the roller and the base.

Through the provision of a gap together with the application of a roller surface speed which is different, preferably greater, than the speed of the web, during process operation a continuous and visually uniform layer of powder builds up rapidly on the outer surface of the roller. The presence of a continuous and visually uniform powder layer on the roller, the formation of which is thought to be (although not wishing to be bound by any theory) caused by the shearing action on the powder of the differing speeds of the roller surface and of the web in the presence of the gap between the two, allows for desirably accurate and uniform packing of the powder into the depressions. The formation of this powder layer is further, favourably facilitated through rotation of the roller surface in the same general direction as the web movement. Returning to the exemplary embodiment shown in FIG. 1, it will be appreciated at the very start of filling, as the web (8) and powder (4) passes through the passage (6), the web will move away from the outer surface of the roller (12) towards the base plate (18) to provide a gap (16) between the roller and the web, and (shortly thereafter) once the continuous layer of powder (9) forms the outer surface of the roller, this layer of powder in turn maintains the gap between the roller and web.

The gap width generally tends to affect the thickness of the layer of powder that forms on the rotating roller in the process. Typically, the thickness of the powder layer formed on the roller is similar to the gap width. It will be appreciated that for embodiments employing a base in conjunction with the roller of the powder filling stage to provide a passage and thus the respective positioning of web and roller, as described above or shown in the exemplary embodiment of FIG. 1, the gap width is typically the width of the passage minus the thickness of the web. The selection of the particular gap width depends on a number of factors, such as the properties of the particular powder being filled, the dimensions and pattern of the microdepressions to be filled, and the web thickness and its variation in thickness. For example, micronized albuterol sulfate with a mass median particle diameter of around 2 to 3 microns and with at least 95% of its particles by mass having diameters below 5 microns has been filled satisfactorily into microdepressions of a sheet material of 0.2 mm thickness using a gap width of 0.65 mm, whilst micronized lactose monohydrate of a similar particle size distribution has been satisfactorily filled to the same sheet material at gaps of 0.45 mm and 0.65 mm. Generally, it has been found that the formation of a stable, substantial covering of powder on the roller is desirably facilitated through the application of a gap width of 1.25 mm or less, more desirably 1.00 mm or less and most desirably 0.75 mm or less. In facilitating the maintenance of a stable covering of powder on the roller together with a desirable continuous and smooth process of feeding and filling of the web, the application of a gap width of 0.2 mm or greater is desirable, 0.3 mm or greater more desirable and 0.4 mm or greater most desirable. As mentioned above, the inclusion of an element of flexibility in positioning of the roller and web has been found to be advantageous, so that the gap is variable in width. For example to facilitate the prevention of the formation of high pressures at the roller, due to powder accumulating at the gap, the positioning of roller and web may be arranged in such a way that the gap is biased towards a pre-determined minimum width, for example through the use of springs, but at the same allowing some variability in the gap width, e.g. movement towards a greater gap width.

The formation of a stable, substantial covering of powder on the roller is, desirably, further facilitated through the provision of a roller surface speed that is greater than the web speed at the position of the roller. Also it has been found that in order to minimize the risk of blocking of powder in the gap (and the risk of consequent failure of the process and possible breakage of the web), the use of a roller surface speed that exceeds the speed of the web by a minimum factor of 1.1 (i.e. by a ratio of at least 1.1 to 1) is advantageous. It has been found that an optimum speed ratio regime depends on a number of factors, such as web speed, the roller diameter, powder characteristics, web surface characteristics, and the gap width. For example, it has been noted that as the web speed increases the optimal ratio of roller surface speed to web speed increases. In general, a ratio of roller surface speed to web speed of at least 1.1 to 1 is suitable, at least 2 to 1 is more suitable and at least 3 to 1 is most suitable. For overall process stability, it has been found to be advantageous to apply a ratio of roller surface speed to web speed of at most 10 to 1 or less, more suitably at most 7 to 1, and most suitably at most 5 to 1.

Web speeds of 3 meters per minutes or more are generally suitable, while for greater production rates and generally better process stability, web speeds of at least 10 meters per minute are desirable, at least 15 meters per minute more desirable, and at least 17 meters per minute most desirable. Generally, a suitable maximum web speed is 25 meters per minutes. For web speeds of around 20 to 25 meters per minute, generally the ratio of roller surface speed to web speed is desirably at least 3:1. To further enhance overall process and filling reliability, it may be desirable to automatically couple the roller surface speed to the web speed. For example through such coupling the optimal and/or desired roller surface speed to web speed ratio can be maintained over changes to the web speed and/or roller surface speed. To minimize any potential tendency to process stalling, for example through blocking of powder at the gap, desirably the web speed is generally maintained without significant speed fluctuations (i.e. with at most 10%, more suitably at most 7%, and most suitably at most 3% fluctuation in speed). It has been found that for a roller having a diameter of 20 mm or greater, the application of web speeds of at least 10 meters per minute enhances the uniformity as well as the stability of the filling process.

Suitably the roller is in its cross-section circular, in particular without any flattened portions. The roller may have a diameter of up to 150 mm. It has been found that smaller diameter rollers are advantageous in providing desirable geometries at the nip of the roller relative to the web and thus desirable shear forces for powder filling. Accordingly, the roller desirably has a diameter of 60 mm or less, more desirably 40 mm or less, even more desirably 30 mm or less and most desirably 25 mm or less. To help minimize centrifugal acceleration at any given roller surface speed (and thus to minimize the potential for powder particles to be propelled from the roller surface as a result of such centrifugal acceleration), it has been found desirable to use a roller with a diameter of 8 mm or more, more desirably 10 mm or more, even more desirably 15 mm or more, and most desirably 20 mm or more.

The surface of the roller is suitably hard and rigid. Rollers may suitably comprise a metal surface, e.g. a solid metal roller or a roller provided with a metal surface. Also it has been found desirable that the surface of the roller is generally smooth, e.g. not engraved, nor provided with a raised structure. For example it has been found that a solid, smooth stainless steel roller is particularly suitable for use in the process. Other materials, such as aluminium alloys, may be used for the roller.

As mentioned previously, for even further enhanced ease in filling as well as enhanced process reliable and stability, it has been found desirable to feed the web to and from the roller such that at the roller the web passes through a bend so that there is a contact angle of less than 180° towards the roller. Here the web is desirably fed to the roller generally along a first plane and from the roller generally along a second plane, the intersection of the first and second planes at the roller defining an angle of less than 180° towards the roller. Referring to the exemplary embodiment in FIG. 1, it can be seen that the overall web movement is from left to right along a horizontal plane as indicated by the arrow (10), and to the roller (12) the web (8) is being fed along the horizontal plane, while from the roller the web is fed along an plane having an upward slope relative to the horizontal. This may be better appreciated from FIG. 2 providing a schematic drawing of just the feed of web (8) to and from the roller (12) of the exemplary embodiment of FIG. 1. (For ease in viewing, the roller is shown in dashed lines, while powder, the base, etc. are not shown at all in the schematic drawing.) Here the web (8) is fed to the roller (12) along a plane labelled A and fed away from the roller along a second plane labelled B, and the intersection of these planes at the roller define a contact angle ($\alpha$) towards the roller, the angle being about 173° in the exemplary embodiment.

Again it is believed that the provision of such a contact angle of less than 180° allows for a partial wrap around of the web at the roller providing a component of force directly normal to the powder layer on the roller. Moreover it is believed that when the web passes through a bend at the roller, e.g. a contact angle less than 180°, more preferably 177° or less, most preferably 175° or less, then a force is contributed to the filling process by the web tension, as a component of the web tension normal to the powder covering layer on the roller, and that this enhances filling and process reliability and stability. Smaller contact angles generally confer greater stability to the filling process. However to minimize friction, component wear, and the risk of web breakage, desirably the contact angle is 150° or greater, more desirably 160° or greater and most desirably 170° or greater.

Figure 2:
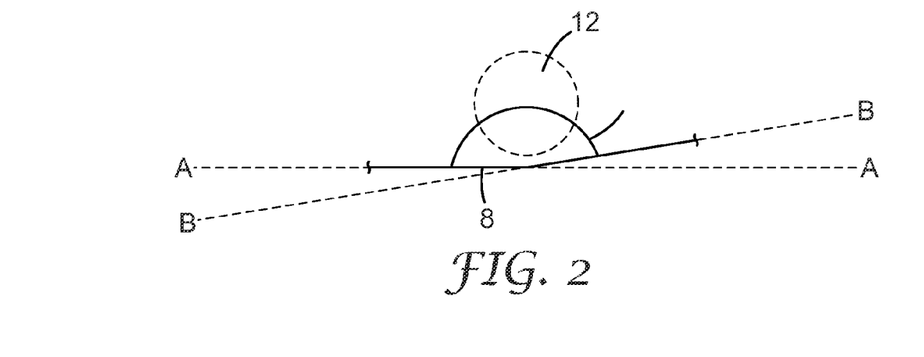
Figure 3:
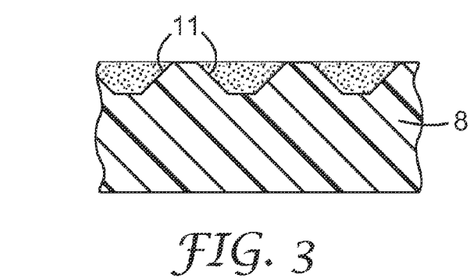

It is to be appreciated that the provision of the desired contact angle can be achieved by using other configurations of feeding the web to and from the roller than that in FIGS. 1 and 2, which show the web being fed to the roller along a horizontal plane and away from the roller along a plane having an upward slope relative to the horizontal. For example, the web may be fed to the roller along a plane having a downward slope relative to the horizontal (e.g. at a 4° difference to the horizontal) and fed from the roller along the horizontal (i.e. 0° difference to horizontal) or along a plane having an upward slope relative to the horizontal (e.g. at a 8° difference to the horizontal) to provide a contact angle less than 180° towards the roller (e.g. a contact angle of 176° or 168°, respectively). It is possible to feed the web from the roller along a plane having a downward slope relative to the horizontal (e.g. at a 5° difference to the horizontal), when the web is fed to the roller along a plane having a downward slope to the horizontal at an appropriate slope (e.g. at 15° difference to the horizontal) so as to provide a contact angle less than 180° towards the roller (e.g. a contact angle of 170°). Correspondingly it is also possible to feed the web to the roller along a plane having an upward slope relative to the horizontal (e.g. at a 5° difference to the horizontal), when the web is fed from the roller along a plane having an upward slope relative to the horizontal at an appropriate slope (e.g. at a 13° difference to the horizontal) so as to provide a contact angle less than 180° towards the roller (e.g. a contact angle of 172°).

It will be appreciated that for a given powdered material to be filled into microdepressions of a particular web, some basic experimentation may be used to determine suitable combinations of process variables such as gap width, web speed, roller surface speed and roller diameter and, if applicable contact angle and web tension. For example, to fill micronized albuterol sulfate powder with a mass median particle diameter of around 2 to 3 microns and with at least 95% of its particles by mass having diameters below 5 microns into discrete micro-depressions (50 microns deep and 140 microns wide at the top surface) in 0.2 mm thick LDPE (low density polyethylene)-coated kraft paper web, the use of a web speed of 10 meters per minute together with a 23 mm diameter polished stainless steel roller rotating with surface speed of about 3.5 times the web speed, a gap width of 0.65 mm and a contact angle of about 171.5° with the web being fed to the roller horizontally provide a stable, robust process with desirably accurate and uniform filling of the microdepressions.

Processes herein suitably include or may include a further step of removing from the surface of the web excess powder not filled within the depressions and remaining on areas of the surface between the depressions. Such removal can be achieved for example by using one or more doctor blades to scrape off residual powder remaining on the surface of the web between the depressions. Such doctor blades may be suitably made of metal (e.g. stainless steel), polymeric (e.g. polyethylene) and/or elastomeric (thermoplastic or thermoset elastomeric) materials. Conveniently they comprise flexible rubber sheets of thickness in the range 1 to 3 mm, supported at an angle to the moving web. An angle in the range of 10° to 60° to the web may be preferably, more particularly 40° to 50°.

Conveniently, the rubber sheets may be held between parallel rigid plates, with a portion of their length protruding. An arrangement of rubber doctor blade wipers contacting the top surface of the moving web sheet material is shown in the exemplary embodiment of FIG. 1. The web (8) moves in the direction of arrow (10) underneath two doctor blades (20, 30). Each doctor blade wiper (31), which may be a nitrile rubber sheet of 1.5 mm thickness and about 70 Shore 'A' hardness, is desirably held between rigid plates (34, 36). The plate towards the web (34) generally has a bevel, to ensure it cannot contact and damage the web. The doctor blade wiper (31) desirably protrudes about 3 mm to 6 mm past the end of the plate towards the web (34) and about 6 mm past the end of the other plate (36), the plates being at an angle of 45° to the web, and their vertical height relative to the web being chosen to ensure good contact of the cleaning edge (32) of the doctor blade wiper (31) with the web whilst avoiding excessive frictional forces on the web. It will be apparent, however, that many alternative arrangements might be envisaged. Vacuum extraction of removed powder from around the edges (32) of the doctor blade wiper (31) may conveniently be used to ensure the process continues uniformly and consistently to remove excess powder. The collected powder may be recycled to the front end of the process for types of powder that are not degraded or altered by passage through the process. As can be appreciated from FIG. 1, it may be desirable to use a doctor blade (40) on the lower surface of the web to remove any powder that may have settled onto the lower surface of the web during processing. Two blades above the web, with one beneath it positioned between them, have been found to be particularly satisfactory. Their positions and heights may preferably be chosen to ensure good contact of the web with each, whilst keeping vertical bending or diversion of the web to a minimum, to avoid large frictional and other forces. Generally the filled web is fed continuously to and through the excess powder removal arrangement or stage.

If desired and/or needed, processes may additionally comprise means to subsequently slit and/or cut the powder filled web to desired widths and/or lengths, for example to provide a tape. Any one of a variety of such means may be employed, such as shear slitting knives, or crush slitting knives or in particular rotating shear slitting knives. It will be appreciated that such slitting and/or cutting can be carried out as in-line process step(s) after filling, and typically after the removal of excess powder. Alternatively such slitting and/or cutting can be carried out as off-line process step(s), where for example the filled web is stored on a jumbo roll and transferred to a separate unit for slitting and/cutting. In both cases, it is desirable that the filled web is fed continuously to and through the slitting and/or cutting arrangement(s) or stage(s).

Preferably, the ratio of length to width is greater than 5:1, more preferably greater than 10:1 and most preferably between 100:1 and 1000:1. Preferably elongate carriers and/or tapes will have a width of about 0.5 to 3 cm and more preferably about 1 to 2 cm. Filled webs and/or elongate carriers (e.g. in the form of a tape) may be provided wound on a spool or provided in the form of a roll.

Processes may also comprise means to control the ambient temperature or relative humidity of the environment in which powder application takes place. This might be particularly relevant when moisture-sensitive powders are to be applied to the web. Suitably, the web filling process might then be carried out in an enclosure of controlled temperature and relative humidity to suit the powdered material being used. Such an enclosure could be sized to just include the powder feeding and filling equipment, with the web being fed into the enclosure through one narrow slit and out to slitting knives via another. It might prove expedient to fit air handling and filtration apparatus to the enclosure, in order to protect operators from potential exposure to any harmful dusts. In addition, means to control the electrostatic charge present on the web or on the powder may be employed. For example, a de-ionizer fan, such as those available from 3M Corporation, may be arranged to blow upon the moving web prior to it reaching the powder feeding point.

Arrangements used to transport the web through the process, together with the arrangement of the driven roller of the powder filling stage as well as other structural elements (e.g. solid base or doctor blades) are generally and suitably chosen to minimize the variation in web tension across the width of the web. Also in the event that the web is slit into elongate carriers, it is desirable to control the tension of such slit carriers, in order to help maintain a uniform tension across the entire web further upstream, e.g. at the point where the web is being filled with powder. Means to control web tension are well known to those skilled in the art. In addition, laterally varying bending, folding or crinkling of the web as well as excessive web edge vibration may be generally avoided through the use by appropriate arrangements of the web path and appropriate control of the web steering.

Finely divided powders generally are well held within the microdepressions (possibly by a combination of electrostatic attraction, Van der Waals forces, physical attraction and, depending upon the configuration of the depression itself, mechanical binding or wedging) such that a cover layer over the filled microdepression is generally not necessary to ensure that powder remains in the microdepressions. However, if desired and/or needed for extra protection the process may include covering and/or sealing the surface of the web with powder-filled microdepressions. This can be achieved by affixing a suitable sheet material to the surface of the web. Additionally or alternatively, storing the web or elongate carrier in a rolled state will in effect seal the top of the depressions through contact with the back-side of the web or elongate carrier itself in the next winding of the roll.

Finely divided powders used in the processes and methods described herein generally have a mass median particle diameter typically 10 microns or less. More suitably, said mass median diameter is 7 microns or less, even more suitably 5 microns or less, and most suitably said mass median diameter is in the range 1 to 3 microns, with at least 90% by mass of the particles having diameters below 5 microns.

The powders may be micronized, e.g. by using a fluid energy mill driven by compressed air, such as shown in 'Drug Delivery to the Respiratory Tract' ed. D. Ganderton and T. Jones, publ. Ellis Horwood, Chichester (1987) pages 89-90, or by repeated stepwise millings or by use of a closed loop milling system.

Processes and methods described herein are particular suited to filling webs and/or manufacturing elongate carriers filled with biologically active substances, such as medicaments, agrochemicals, or cosmetic products. A biologically active substance may be, for example, a drug, a vitamin or a vaccine. Powders used may be a biologically active substance in itself (e.g. micronized drug particles) or may be a carrier substance with a biologically active substance incorporated therein or thereon (e.g. mixtures of micronized drug particles with micronized lactose bulking agents or other excipients, mixtures of more than one micronized drug, coated particles of spray-dried drug, or microcapsules).

Moreover filled webs and/or elongate carriers as provided by processes and methods disclosed herein, including well-controlled metered and small quantities of a biologically active substance may be advantageously utilized as such or as part of delivery systems for the administration of such powdered biologically active substances orally (e.g. using biodegradable and/or digestible web material) or topically (e.g. provided as part of a medical or surgical tape, drape, dressing and/or bandage) or through transdermal, transmucosal, (e.g. buccal, sublingual) vaginal, rectal, ocular or aural delivery for use with humans or animals.

Such prepared filled webs and/or elongate carriers are also well suited for application of measured quantities of powdered, biologically active substances in the field of agriculture, e.g. delivery of growth regulators, pesticides, fungicides or other agrochemicals.

Filled webs and/or elongate carriers as provided by processes disclosed herein are particularly suited for delivering medicaments for inhalation by a patient. Filled webs and/or elongate carriers preferably will provide consistent release of the medicament when exposed to the force used to aerosolize the medicament. In a preferred embodiment of an aerosol device, the finely divided (e.g. micronized) medicament is aerosolized in an unagglomerated state by impaction on the back-side of the sheet material. Suitable devices for aerosolizing the medicament are disclosed in U.S. Pat. Nos. 5,408,994 and 5,619,984, incorporated herein by reference. Other suitable devices employing means other than impaction to aerosolize the medicament from filled webs and/or elongate carriers are disclosed in U.S. Pat. No. 5,619,984. The filled web and/or elongate carrier will be preferably in the form of a tape that is contained within a cassette and is advanced dose by dose as required by the patient.

Typically, an area of elongate carrier or tape of 20 mm length and 10 mm width per single dose is suitable for use in a dry powder inhaler. Typically, such a dose area might have 200 to 2000 discrete microdepressions, each of about 45 microns depth and about 150 microns diameter. Advantageously, the rows of micro-depressions along the longitudinal axis of the elongate carrier or tape do not lie exactly parallel with the axis, but instead lie skewed at a small angle (e.g. 0.5° to) 2° to it, in order to avoid "quantization effects" caused by lateral variability in the slitting positions. (The skew angle can be chosen appropriate to the microdepression spacing distance and the desired slit width, such that an exact total microdepression volume is present on each (e.g. 20 mm×10 mm) dose area, no matter where slitting occurs, laterally.) For use in dry powder inhalers, preferably, the microdepressions are provided by cast embossing of a low density polyethylene (LDPE) layer using a photolithographically patterned and etched, or a diamond machined, patterning roller. Suitably the aforesaid LDPE layer is provided on a paper backing or a paper/LDPE laminate backing (with the paper between the two LDPE layers).

For delivery by inhalation, suitable medicaments include any drug or drugs combination that may be administered by inhalation, that is a solid or that may be incorporated in a solid carrier. Suitable drugs include those for the treatment of respiratory disorders, e.g., bronchodilators, corticosteroids and drugs for the prophylaxis of asthma. Other drugs such as anorectics, anti-depressants, anti-hypertensive agents, antineoplastic agents, anti-cholinergic agents, dopaminergic agents, narcotic analgesics, beta-adrenergic blocking agents, prostaglandins, sympathomimetics, tranquilizers, steroids, vitamins and sex hormones may be employed for delivery by inhalation. Antianginals, antibacterials, antibiotics, antiinflammatories, anti-migraine drugs, anti-peptics, antivirals, cardiovascular drugs, hypoglaecemics, immunomodulators, lung surfactants, and vaccines may similarly be employed.

It is preferred for delivery by inhalation that the medicament employed exhibits a potency which permits a single dose to be loaded onto the web and/or elongate carrier in an area of less than about 25 $cm^2$ and preferably less than about 5 $cm^2$. More preferred is a web and/or elongate carrier containing a drug in such a manner and of such a type that between 0.25 and 2.5 $cm^2$, most preferably between 1.5 and 2.25 $cm^2$, of the web and/or elongate carrier will contain a single dose when used in a device such as those described in U.S. Pat. Nos. 5,408,994 or 5,619,984. Stated differently, given that a filled web and/or elongate carrier may conveniently carry between about 25 and 500 μg of powder per $cm^2$, the potency of the medicament will preferably be such that a single dose may be carried on the above-stated 0.25 to 2.5 $cm^2$ of web and/or elongate carrier.

Exemplary drugs which may be employed for delivery by inhalation include but are not limited to: albuterol, terbutaline, fenoterol, metaproterenol, isoproterenol, isoetharine, bitolterol, epinephrine, tulobuterol, bambuterol, reproterol, adrenaline, ipratropium, oxitropium, tiotropium, beclomethasone, betamethasone, flunisolide, budesonide, mometasone, ciclesonide, rofleponide, aminophylline, dyphylline, theophylline, cromolyn sodium, nedocromil sodium, ketotifen, azelastine, ergotamine, cyclosporine, salmeterol, fluticasone, formoterol, procaterol, indacaterol, TA2005, omalizumab, montelukast, zafirlukast, betamethasone sodium phosphate, dexamethasone, dexamethasone sodium phosphate, dexamethasone acetate, prednisone, methylprednisolone acetate, zileuton, insulin, atropine, prednisolone, benzphetamine, chlorphentermine, amitriptyline, imipramine, clonidine, actinomycin c, bromocriptine, buprenorphine, pentamidine, calcitonin, leuprolide, alpha-1-antitrypsin, interferons, propranolol, lacicortone, triamcinolone, dinoprost, xylometazoline, diazepam, lorazepam, folic acid, nicotinamide, clenbuterol, ethinyloestradiol, levonorgestrel, and pharmaceutically acceptable salts and esters thereof such as albuterol sulfate, formoterol fumarate, salmeterol hydroxynaphthoate, beclomethasone dipropionate, triamcinolone acetonide, fluticasone propionate, tiotropium bromide, leuprolide acetate and mometasone furoate.

Further drugs that may also be delivered by inhalation include but are not limited to aspirin, acetaminophen, ibuprofen, naproxen sodium, buprenorphine hydrochloride, propoxyphene hydrochloride, propoxyphene napsylate, meperidine hydrochloride, hydromorphone hydrochloride, morphine sulfate, fentanyl citrate, oxycodone hydrochloride, codeine phosphate, dihydrocodeine bitartrate, pentazocine hydrochloride, hydrocodone bitartrate, levorphanol tartrate, diflunisal, diamorphine, trolamine salicylate, methadone hydrochloride, nalbuphine hydrochloride, nalorphine, tetrahydrocannabinol, mefenamic acid, butorphanol tartrate, choline salicylate, butalbital, phenyltoloxamine citrate, diphenhydramine citrate, methotrimeprazine, cinnamedrine hydrochloride, meprobamate, ergotamine tartrate, propanolol hydrochloride, isometheptene mucate, dichloralphenazone, sumatriptan, rizatriptan, zolmitriptan, naratriptan, eletriptan, barbiturates (e.g., pentobarbital, pentobarbital sodium, secobarbital sodium), benzodiazapines (e.g., flurazepam hydrochloride, triazolam, tomazeparm, midazolam hydrochloride, lorazepam, buspirone hydrochloride, prazepam, chlordiazepoxide hydrochloride, oxazepam, clorazepate dipotassium, diazepam, temazepam), lidocaine, prilocaine, xylocaine, beta-adrenergic blockers, calcium channel blockers (e.g., nifedipine, diltiazem hydrochloride, and the like), nitrates (e.g., nitroglycerin, isosorbide dinitrate, pentaerythritol tetranitrate, erythrityl tetranitrate), hydroxyzine pamoate, hydroxyzine hydrochloride, alprazolam, droperidol, halazepam, chlormezanone, haloperidol, loxapine succinate, loxapine hydrochloride, thioridazine, thioridazine hydrochloride, thiothixene, fluphenazine hydrochloride, fluphenazine decanoate, fluphenazine enanthate, trifluoperazine hydrochloride, chlorpromazine hydrochloride, perphenazine, lithium citrate, prochlorperazine, lithium carbonate, bretylium tosylate, esmolol hydrochloride, verapamil hydrochloride, amiodarone, encainide hydrochloride, digoxin, digitoxin, mexiletine hydrochloride, disopyramide phosphate, procainamide hydrochloride, quinidine sulfate, quinidine gluconate, quinidine polygalacturonate, flecainide acetate, tocainide hydrochloride, lidocaine hydrochloride, phenylbutazone, sulindac, penicillamine, salsalate, piroxicam, azathioprine, indomethacin, meclofenamate sodium, gold sodium thiomalate, ketoprofen, auranofin, aurothioglucose, tolmetin sodium, colchicine, allopurinol, heparin, heparin sodium, warfarin sodium, urokinase, streptokinase, altoplase, aminocaproic acid, pentoxifylline, empirin, ascriptin, valproic acid, divalproate sodium, phenytoin, phenytoin sodium, clonazepam, primidone, phenobarbitol, phenobarbitol sodium, carbamazepine, amobarbital sodium, methsuximide, metharbital, mephobarbital, mephenytoin, phensuximide, paramethadione, ethotoin, phenacemide, secobarbitol sodium, clorazepate dipotassium, trimethadione, ethosuximide, doxepin hydrochloride, amoxapine, trazodone hydrochloride, amitriptyline hydrochloride, maprotiline hydrochloride, phenelzine sulfate, desipramine hydrochloride, nortriptyline hydrochloride, tranylcypromine sulfate, fluoxetine hydrochloride, doxepin hydrochloride, imipramine hydrochloride, imipramine pamoate, nortriptyline, amitriptyline hydrochloride, isocarboxazid, desipramine hydrochloride, trimipramine maleate, protriptyline hydrochloride, hydroxyzine hydrochloride, diphenhydramine hydrochloride, chlorpheniramine maleate, brompheniramine maleate, clemastine, azelastine, cyproheptadine hydrochloride, terfenadine citrate, clemastine, triprolidine hydrochloride, carbinoxamine maleate, diphenylpyraline hydrochloride, phenindamine tartrate, lamivudine, abacavir, acyclovir, gancyclovir, valganciclovir, cidofovir, foscarnet, azatadine maleate, tripelennamine hydrochloride, dexchlorpheniramine maleate, methdilazine hydrochloride, trimprazine tartrate, trimethaphan camsylate, phenoxybenzamine hydrochloride, pargyline hydrochloride, deserpidine, diazoxide, guanethidine monosulfate, minoxidil, rescinnamine, sodium nitroprusside, rauwolfia serpentina, alseroxylon, phentolamine mesylate, reserpine, calcitonin, parathyroid hormone, acitretin, amikacin sulfate, aztreonam, benzydamine, calcipotriol, chloramphenicol, chloramphenicol palmitate, chloramphenicol sodium succinate, ciprofloxacin hydrochloride, clindamycin hydrochloride, clindamycin palmitate, clindamycin phosphate, efalizumab, metronidazole, metronidazole hydrochloride, gentamicin sulfate, lincomycin hydrochloride, tobramycin sulfate, tacrolimus, vancomycin hydrochloride, polymyxin B sulfate, colistimethate sodium, colistin sulfate, tetracycline, griseofulvin, keloconazole, interferon gamma, zidovudine, amantadine hydrochloride, ribavirin, acyclovir, pentamidine e.g. pentamidine isoethionate, cephalosporins (e.g., cefazolin sodium, cephradine, cefaclor, cephapirin sodium, ceftizoxime sodium, cefoperazone sodium, cefotetan disodium, cefutoxime axotil, cefotaxime sodium, cefadroxil monohydrate, ceftazidime, cephalexin, cephalothin sodium, cephalexin hydrochloride monohydrate, cefamandole nafate, cefoxitin sodium, cefonicid sodium, ceforanide, ceftriaxone sodium, ceftazidime, cefadroxil, cephradine, cefuroxime sodium, and the like), penicillins (e.g., ampicillin, amoxicillin, penicillin G benzathine, cyclacillin, ampicillin sodium, penicillin G potassium, penicillin V potassium, piperacillin sodium, oxacillin sodium, bacampicillin hydrochloride, cloxacillin sodium, ticarcillin disodium, azlocillin sodium, carbenicillin indanyl sodium, penicillin G potassium, penicillin G procaine, methicillin sodium, nafcillin sodium, and the like), erythromycins (e.g., erythromycin ethylsuccinate, erythromycin, erythromycin estolate, erythromycin lactobionate, erythromycin siearate, erythromycin ethylsuccinate, and the like), tetracyclines (e.g., tetracycline hydrochloride, doxycycline hyclate, minocycline hydrochloride, GM-CSF, ephedrine, pseudoephedrine, ammonium chloride, androgens (e.g., danazol, testosterone cypionate, fluoxymesterone, ethyltostosterone, testosterone enanihate, methyltestosterone, fluoxymesterone, testosterone cypionate), estrogens (e.g., estradiol, estropipate, conjugated estrogens), progestins (e.g., methoxyprogesterone acetate, norethindrone acetate), levothyroxine sodium, human insulin, purified beef insulin, purified pork insulin, glyburide, chlorpropamide, glipizide, tolbutamide, tolazamide, rosiglitazone, pioglitazone, troglitazone, clofibrate, dextrothyroxine sodium, probucol, lovastatin, rosuvastatin, niacin, DNase, alginase, superoxide dismutase, lipase, calcitonion, alpha-1-antitrypsin, interferons, sense or anti-sense nucleic acids encoding any protein suitable for delivery by inhalation, erythropoietin, famotidine, cimetidine, ranitidine hydrochloride, omeprazole, esomeprazole, lanzoprazole, meclizine hydrochloride, nabilone, prochlorperazine, dimenhydrinate, promethazine hydrochloride, thiethylperazine, scopolamine, sildenafil, vardenafil, cilomilast, imiquimod or resiquimod. Where appropriate, these drugs may be delivered in alternative salts forms.

The medicament may comprise one or more drugs, having one or more particulate forms, and may include one or more physiologically acceptable or inert excipients.

The invention claimed is:

1. A method for filling a plurality of microdepressions in a major surface of a web, said microdepressions having a depth of about 5 to 500 microns but less than the thickness of the web and an opening at the surface of the web of about 10 to 500 microns in width, with finely divided powder, said process comprising:

continuously feeding the web to and through a powder filling stage;

at the powder filling stage, filling the powder into said microdepressions on the surface of the web using a driven roller, wherein said roller is rotating about an axis generally transverse to said direction of web movement, while the surface speed of the roller and the web speed are different and wherein the roller and web are positioned relative to one another, such that between the upper surface of the web and the outer surface of the roller there is a gap;

wherein the powder is fed either onto the web upstream of the roller of the powder filling stage or to the roller of the powder filling stage; and wherein the method further comprises sensing accumulation of powder on the roller and/or on the web upstream of the roller and in response to said sensing automatically controlling the powder feed.

2. A method according to claim 1, further comprising the step of removing from said surface of the web excess powder not filled within the depressions and remaining on areas of the surface between the depressions.

3. A method according to claim 1, further comprising step(s) of slitting and/or cutting the filled web in predetermined widths and/or predetermined lengths.

4. A method according to claim 1, wherein said roller is rotating in the same direction as the web movement.

5. A method according to claim 1, wherein the surface speed of the roller is greater than the web speed.

6. A method according to claim 5, wherein the ratio of the roller surface speed to the web speed is at least 3 to 1.

7. A method according to claim 5, wherein the ratio of the roller surface speed to the web speed is at most 5 to 1.

8. A method according to claim 1, wherein the gap is 1.25 mm or less.

9. A method according to claim 1, wherein the web is fed to the roller generally along a first plane and fed from the roller generally along a second plane, such that at the roller the web passes through a bend, wherein the first plane and the second plane define an angle of less than 180° towards the roller.

10. A method according to claim 9, wherein the first plane and second plane define an angle of 160° or greater towards the roller.

11. A method according to claim 1, wherein powder is fed either onto the web upstream of the roller or to the roller of the powder filling stage, such as to provide an accumulation of powder on the web upstream of and adjacent to the roller.

12. A method according to claim 1, wherein the biologically active substance is a medicament suitable for administration by inhalation.

13. A method of manufacturing an elongate carrier with microdepressions containing finely divided powder said process comprising:

providing a web comprising a plurality of microdepressions in a major surface of the web, said microdepressions having a depth of about 5 to 500 microns but less than the thickness of the web and an opening at the surface of the web of about 10 to 500 microns in width, continuously feeding the web to and through a powder filling stage at the powder filling stage, filling the powder into said microdepressions on the surface of the web using a driven roller, wherein said roller is rotating about an axis generally transverse to said direction of web movement, while the surface speed of the roller and the web speed are different and wherein the roller and web are positioned relative to one another, such that between the upper surface of the web and the outer surface of the roller there is a gap;

removing from said surface of the web excess powder not filled within the microdepressions and remaining on areas of the surface between the depressions;

and optionally slitting and/or cutting the web in predetermined widths and/or predetermined lengths wherein the powder is fed either onto the web upstream of the roller of the powder filling stage or to the roller of the powder filling stage; and wherein the method further comprises sensing accumulation of powder on the roller and/or on the web upstream of the roller and in response to said sensing automatically controlling the powder feed.

14. An elongate carrier according to claim 13 wound on a spool or in the form of a roll.

15. A dry powder inhaler comprising an elongate carrier according to claim 14.

* * * * *

UNITED STATES PATENT AND TRADEMARK OFFICE
CERTIFICATE OF CORRECTION

PATENT NO. : 8,997,799 B2  
APPLICATION NO. : 12/293683  
DATED : April 7, 2015  
INVENTOR(S) : Hodson et al.

Page 1 of 1

It is certified that error appears in the above-identified patent and that said Letters Patent is hereby corrected as shown below:

On the Title Page

Item (75), should read:  
Peter D. Hodson, Derbyshire (GB);  
Matthew J. Wilby, Leicestershire (GB);  
Richard Peter Glynn Jewell, Saint Lambert (CA)

Signed and Sealed this  
Twenty-seventh Day of October, 2020

Andrei Iancu  
*Director of the United States Patent and Trademark Office*